US012625493B2

(12) United States Patent
Eder et al.

(10) Patent No.: US 12,625,493 B2
(45) Date of Patent: May 12, 2026

(54) MONITORING METHODS, COMPUTER PROGRAM PRODUCT, MONITORING UNIT, GAS ANALYSIS DEVICE, AND USE OF ARTIFICIAL INTELLIGENCE

(71) Applicant: Siemens Aktiengesellschaft, Munich (DE)

(72) Inventors: Jana Eder, Vienna (AT); Simon Weilandt, Neu-Ulm/Stadtmitte (DE); Ralf Bitter, Weingarten (DE); Stephanie Holly, Stockerau (AT); Tim Offermann, Rheinzabern (DE); Daniel Schall, Hollabrunn (AT); Piotr Strauch, Ruelzheim (DE)

(73) Assignee: Siemens Aktiengesellschaft, Munich (DE)

( * ) Notice: Subject to any disclaimer, the term of this patent is extended or adjusted under 35 U.S.C. 154(b) by 18 days.

(21) Appl. No.: 18/874,645

(22) PCT Filed: May 24, 2023

(86) PCT No.: PCT/EP2023/063947
§ 371 (c)(1),
(2) Date: Dec. 13, 2024

(87) PCT Pub. No.: WO2023/241894
PCT Pub. Date: Dec. 21, 2023

(65) Prior Publication Data
US 2025/0164985 A1      May 22, 2025

(30) Foreign Application Priority Data
Jun. 15, 2022    (EP) ..................................... 22179239

(51) Int. Cl.
G05B 23/02        (2006.01)
G01N 33/00        (2006.01)

(52) U.S. Cl.
CPC ....... G05B 23/0254 (2013.01); G01N 33/007 (2013.01)

(58) Field of Classification Search
CPC ........... G06N 3/04; G06N 3/084; G06N 7/01; G06N 3/044; G06N 3/045; G06N 3/0464;
(Continued)

(56) References Cited

U.S. PATENT DOCUMENTS

| | | | |
|---|---|---|---|
| 5,548,597 A | 8/1996 | Kayama et al. | |
| 2012/0041663 A1 | 2/2012 | Suzuki et al. | |

(Continued)

FOREIGN PATENT DOCUMENTS

| | | | |
|---|---|---|---|
| CN | 113204590 | 8/2021 | |
| DE | 4436658 | 4/1995 | |

(Continued)

OTHER PUBLICATIONS

PCT International Search Report and Written Opinion dated Sep. 11, 2023 based on PCT/EP2023/063947 filed May 24, 2023.

*Primary Examiner* — Mohammad K Islam
(74) *Attorney, Agent, or Firm* — Cozen O'Connor

(57)        ABSTRACT

A computer program product, a monitoring unit, gas analysis device equipped with the monitoring unit, use of artificial intelligence for monitoring the gas analysis device, and monitoring methods for a system having a plurality of devices which are configured to provide an associated measured value and/or a control command, wherein the monitoring methods are based on the use of a processing device or a neural network, with which measured values and/or control commands are evaluated.

11 Claims, 3 Drawing Sheets

(58) Field of Classification Search
CPC .......... G06N 3/047; G06N 3/048; G06N 3/08;
G06N 3/0895; G06N 3/09; G06N 3/10;
G06N 5/022; G06N 5/045; G05B
23/0254; G01N 33/007
See application file for complete search history.

(56)                      References Cited

U.S. PATENT DOCUMENTS

| | | | |
|---|---|---|---|
| 2014/0046983 A1* | 2/2014 | Galloway ............. | G06F 16/248 |
| | | | 707/798 |
| 2020/0065677 A1* | 2/2020 | Iriarte Lopez ........... | G06N 3/09 |
| 2020/0310370 A1 | 10/2020 | Bogo et al. | |
| 2022/0084335 A1 | 3/2022 | Tang et al. | |
| 2022/0180154 A1* | 6/2022 | Martinez ................. | G06F 18/24 |
| 2023/0018575 A1* | 1/2023 | Yubo ....................... | G06N 3/045 |
| 2023/0259756 A1* | 8/2023 | Mcthrow ................. | G06N 3/10 |
| | | | 706/11 |

FOREIGN PATENT DOCUMENTS

| | | |
|---|---|---|
| DE | 102020202866 | 9/2021 |
| DE | 102022200694 | 8/2023 |
| EP | 3961333 | 3/2022 |
| KR | 20210147318 | 12/2021 |

* cited by examiner

MONITORING METHODS, COMPUTER PROGRAM PRODUCT, MONITORING UNIT, GAS ANALYSIS DEVICE, AND USE OF ARTIFICIAL INTELLIGENCE

CROSS-REFERENCE TO RELATED APPLICATIONS

This is a U.S. national stage of application No. PCT/EP2023/063947 filed 24 May 2023. Priority is claimed on European Application No. 22179239.3 filed 15 Jun. 2022, the content of which is incorporated herein by reference in its entirety.

BACKGROUND OF THE INVENTION

1. Field of the Invention

The invention relates to a monitoring method for monitoring a system, a computer program product, a monitoring unit which has a corresponding computer program product, a gas analysis device having such a monitoring unit, and further relates to the use of artificial intelligence for monitoring the gas analysis device.

2. Description of the Related Art

Printed publication KR 2021147318 A discloses a multi-sensor-based artificial intelligence that is designed for error diagnosis in a mechanical device. Sensor data is collected therein and is processed by means of an autoencoder.

US Pub. No. 2020/0310370 A1 discloses a control system having an autoencoder, in which sensor data is processed into derived sensor data. The autoencoder receives the derived sensor data and from it determines a prediction. Based on the prediction, a control intervention is triggered.

In various automation technology applications, increasingly complex systems with an increasing number of individual devices are being employed. The aim is also to have a flexible operation for processing different input materials. As a result of the increasing complexity of operations and systems, monitoring such systems is becoming more demanding.

SUMMARY OF THE INVENTION

In view of the foregoing there is therefore a need for a facility for monitoring complex systems that offers reliable automatic error detection and that can be quickly adapted to changing operational requirements. This applies in particular for gas analysis devices, which are becoming increasingly more complex and sensitive due to increasing demands on measurement accuracy.

The objects and advantages are achieved in accordance with the invention by a monitoring method for monitoring an operation of a system that comprises a plurality of devices that are each configured to provide a measured value and/or a control command. The devices can, for example, be sensors, control units, regulation units or combinations thereof. The measured values can be captured physical variables or information about the state of the respective device. The monitoring method comprises a first step, in which an input signal array is provided that comprises a plurality of cells. A cell of the input signal array is suitable for receiving a specified measured value or control command and for passing it to a further processing unit. The input signal array can be formed as a one-, two- or higherdimensional array, i.e., a data field. Furthermore, in the first step a monitoring data array is provided, which corresponds to the input signal array in terms of dimensionality and size, i.e., the number of cells. In each case, a cell of the input signal array corresponds to a cell of the monitoring data array.

The monitoring method also has a second step, in which the system is provided in an active operating state. In the active operating state, measured values or control commands are generated essentially continuously and are provided for the monitoring method for further processing. The captured measured values and/or control commands are transferred to the input signal array and are fed into the corresponding associated cells as contents. With the further processing unit, these are processed into contents of corresponding cells in the monitoring data array.

In a third step, a system deviation parameter is determined based on the second step into the input signal array. The system deviation parameter is formed by a plurality of cells of the monitoring data array. The system deviation parameter can, for example, be formed as a sum of contents of cells of the monitoring data array or as a sum of squared contents of the cells of the monitoring data array. The contents of the cells of the monitoring data array can each be standardized to a reference value individually or as several together. The contents are configured to be type-compatible with contents of the corresponding cells of the input signal array. A weighting of individual cells of the monitoring data array is also possible. The weighting can be performed by an algorithm before or during the operational sequence of the monitoring method. If the system deviation parameter exceeds an adjustable system threshold value in the third step, the presence of an abnormal state is identified.

The monitoring method further has a fourth step, which can be performed if an abnormal operating state of the system is identified in the third step. Here, the contents of the cells of the monitoring data array combined in the system deviation parameter are further processed separately. Using contents of the cells of the monitoring data array and contents of corresponding cells of the input signal array, cell deviation parameters are determined in pairs. This can occur, for example, by calculating a difference. Further, in the fourth step a cell of the input signal array or of the monitoring data array is identified as a defective cell if the amount of an associated cell deviation parameter exceeds an adjustable cell threshold value. The cell threshold value can be specified by a user, a table, an algorithm, or artificial intelligence. The defective cell can in this case be a cell of the input signal array or a cell of the monitoring data array. Thus, an associated device can be identified as defective. In particular, a component of a device can be identified as defective. Furthermore, in the inventive monitoring method, a warning is issued if a defective cell is identified. The warning can be established as a visual or acoustic warning to a user and/or as an electronic warning signal, for example, to a control unit of the system. Using an electronic control signal, a countermeasure can be initiated by the control unit in the operation of the system.

The inventive monitoring method is essentially constructed in two stages. Firstly, using the second and third steps it is identified whether in fact an abnormal operating state is present. Only if an abnormal operating state is identified is an analysis made by separately capturing and evaluating cell deviation parameters individually, in order thus to identify a defective cell and thereby to obtain a detailed picture of the abnormal operating state that is present. As long as a normal operating state is present, the third step only entails a matching between the system deviation parameter and the system threshold value. Accordingly, in the normal operating state the number of compute-intensive comparison operations to be performed is minimized. The system deviation parameter can, for example, be established as a sum of cell deviation parameters, which can be determined with reduced computational effort. Only when an abnormal operating state is identified does an increased number of comparison operations occur using the cell deviation parameters and the associated cell threshold values. The inventive monitoring method can consequently be performed with a reduced computing power. The inventive monitoring method, in particular the second, third and fourth steps, in consequence offers real-time capability for a broad range of systems. The term "real-time capability" is here to be understood in the respective sense of the corresponding system. The invention is based on, among other things, the recognition that the system deviation parameter in the third step can be reliably employed as a decision criterion for the performance of the fourth step. The inventive monitoring method overall offers increased reliability with a reduced computational effort.

One embodiment of the inventive monitoring method comprises a fifth step, in which a defective cell determined in the fourth step or a determined set of defective cells are used further. In the fifth step, the defective cell or the set of defective cells is captured and evaluated by pattern matching. With the pattern matching the cause of the defect is determined in the fifth step. To this end, a database containing a plurality of stored comparison patterns of different damage states, i.e., abnormal operating states of the system, can be employed. Alternatively or additionally, the pattern matching can also be performed via artificial intelligence, for example, a machine-learning algorithm, which is trained before and/or during the operation of the system. During pattern matching, it is also possible to take account for one or more defective cells of the extent to which, i.e., in which amount, these exceed the amount of the associated cell threshold value. The cause of the defect can, for example, be a defective device in the system, a loss of a functionality of such a device or an external influence on the system. The inventive monitoring method can be performed with reduced computing power or can be performed quickly with increased computing power. As a result, such artificial intelligence can be further developed, in particular further trained, concurrently with the operation of the system. The inventive monitoring method as a result offers an improved recognition of abnormal operating states of the system.

Further, in the monitoring method the first, second, third and/or fourth step can be performed via an autoencoder. The system deviation parameter, which is thus determined via the autoencoder, can be "a total reconstruction error". Autoencoders are available in different configurations and have an increased degree of reliability and robustness. Furthermore, autoencoders are powerful and enable a large amount of input data, i.e., from extensive input signal arrays, to be processed quickly. The inventive monitoring method is consequently easy to implement and can be adapted to different systems. Further, the autoencoder enables a plurality of steps of the inventive monitoring method to be executed. Furthermore, what is known as unsupervised learning is possible with an autoencoder. A dataset for training the autoencoder manages with a simplified sorting, from a reduced data labeling. Furthermore, in a normal operating state the autoencoder uses the relationship between existing current data. The use of an extensive database is therefore unnecessary for the majority of the operating time.

In addition, at least one of the adjustable cell threshold values can be established in the inventive monitoring method as a fixed threshold value or as a moving threshold value. A fixed threshold value offers simple configurability of the monitoring method. For cell threshold values that are standardized to a reference value, the inventive monitoring method can easily be configured by at least one fixed threshold value, such as during an initialization. In contrast, a moving threshold value, for example, enables account to be taken of a degradation effect on a device, and thus on a corresponding cell of the input signal array. For example, the cell threshold value can increase or decrease along a function depending on the number of hours a device has been operating. As a result, inappropriate warnings are prevented and/or premature degradations of devices are reliably identified. The diagnostic accuracy of the claimed inventive monitoring method is thus further increased. For example, the threshold value can be an adjustable multiple of a standard deviation of the corresponding data and/or an adjustable multiple of a mean total reconstruction error. As a result, both a fixed and a moving threshold value can be provided. Whether the threshold value is moving or fixed depends on whether the underlying values, for example, the standard deviation or the mean total reconstruction error, are maintained during the inventive monitoring method.

In a further embodiment of the inventive monitoring method, the second step can comprise an interpolation of measured values and/or control commands, passed to the input signal array. The input signal array is thereby provided with synchronous measurement points, so that every input of the input signal array describes an operating state of the system in a specific discrete time interval. As a result, an increased temporal resolution can be achieved by the inventive monitoring method. Ambiguities or inconsistencies in inputs into the input signal array during transient operating states of the system, and thus inappropriate warnings, are thus minimized. The interpolation can be established in the form of "upsampling". As a consequence, the inventive monitoring method is suitable for time-critical applications, in which accelerated responses to the present operating state are offered. The inventive monitoring method thereby has increased reliability and diagnostic accuracy. Alternatively, "downsampling" can also occur in the second step. This means that only those measured values and/or control commands are passed to the input signal array that already lie in a discrete time interval. As a result, the computing power required for the inventive monitoring method is reduced.

Furthermore, the input signal array and/or the monitoring data array can comprise cells in which measured values and/or control commands that satisfy an adjustable relevance criterion are stored during the inventive monitoring method. The relevance criterion can, for example, be an indication of how many known defects in the corresponding cell are expected to cause the cell threshold value to be exceeded. A cell that with a minimum number of known defects, in particular with no known defect, exceeds the amount of the cell threshold value can be removed from the input signal array. The inventive monitoring method can consequently further optimize itself automatically, and thus speed up, as the operating time progresses. Among other things, this allows the system to be modified easily, without the modifications performed impinging on the performance of the inventive monitoring method. The relevance criterion can in particular be employed for "pruning", for example, of the input signal array.

The underlying object and advantages in accordance with the invention are similarly achieved by a further inventive monitoring method. The monitoring method serves to monitor a system that has a plurality of devices that interact for the normal operation of the system. The devices can, for example, be sensors, control units, regulation units or combinations thereof. The devices are configured to form nodes in a neural network that maps the interaction of the devices in the system. The neural network comprises zero correlations and/or operating correlations. The devices can be physically separate devices, or different functionalities in physically separate devices. The monitoring method comprises a first step, in which a trained neural network is provided, which has a plurality of edges, each of which corresponds to a zero correlation or an operating correlation between two nodes of the neural network. The nodes are here formed by devices of the system. A zero correlation is to be understood as a correlation with a correlation value that lies below an adjustable correlation threshold value. A "zero correlation" describes a weak, negligible or non-existent relationship between two nodes. The term zero correlation is to be understood within the meaning of the previously unpublished German patent application bearing the official file number DE 10 2022 200 694.1, the disclosure of which is incorporated herein by reference in its entirety. In the provided trained neural network, the zero correlations have correlation values that lie below the adjustable correlation threshold value. The corresponding correlation values are determined during training of the neural network. The zero correlations thus describe pairs of devices, between which no identifiable relationship is to be expected in a normal operating state.

Operating correlations are to be understood as correlations in which there is a sufficiently strong relationship between two nodes. An operating correlation is consequently the opposite or counterpart of a zero correlation. The term operating correlation is to be understood as corresponding to the term zero correlation in accordance with application DE 10 2022 200 694.1.

Furthermore, the monitoring method comprises a second step, in which the system is provided in an active operating state and measured values and/or control commands that occur in the active operating state are captured. The measured values can be captured physical variables or information about the state of the respective device. The captured measured values and/or control commands each correspond to at least one node and/or one edge of the neural network. The captured measured values and/or control commands are suitable for use as input for the neural network.

In a third step, a network deviation parameter is determined, which combines correlation values of a plurality of edges of the neural network. To this end, correlation values are determined for multiple edges on the basis of the measured values and/or control commands captured in the second step, which are then combined in a sum, for example, in terms of amount. The correlation values can be captured for edges of zero correlations and/or of operating correlations in order to determine the network deviation parameter. The network deviation parameter thus represents a compressed variable, which maps an overall state of the system. This is followed by a fourth step, in which an abnormal operating state of the system is identified if the network deviation parameter exceeds the amount of an adjustable network threshold value.

The network threshold value can be specified by a user or an algorithm and represents a measure that maps a deviation from a desired target state of the system. If the network threshold value is exceeded or undershot, then this is consequently caused by the fact that correlation values of edges, which are normally zero correlations, increase such that they can no longer accurately be categorized as zero correlations individually or in combination. The inventive monitoring method thus identifies the presence of apparent correlations, where in a normal operating state zero correlations exist or should exist. Alternatively or additionally, operating correlations can also have deviations that, in combination, result in the network threshold value being exceeded or undershot. The inventive monitoring method is based on, among other things, the surprising finding that abnormal operating states can easily and reliably be identified using zero correlations, which otherwise have no further significance for the operation. More detailed knowledge about the zero correlations is unnecessary, since these are free from underlying physical relationships. Furthermore, edges with zero correlations can be generated in increased numbers, essentially automatically. Similarly, a deviation from operating correlations can easily be identified and an abnormal operating state identified. If the abnormal operating state is identified, then a warning is issued. The warning can be a visual or acoustic warning to a user and/or an electronic warning signal, for example, to a control unit of the system. Using an electronic control signal, a countermeasure can be initiated by the control unit during the operation of the system.

The network deviation parameter can be provided with reduced computational effort and can be checked for the amount by which the network threshold value is exceeded using a minimum of comparison operations. Accordingly, the inventive monitoring method can be performed with reduced computational effort or with increased speed. By way of the first, second, third and fourth step, the real-time capability of the inventive monitoring method is thus increased. Here, the term real-time capability is to be understood in the light of the specific application, i.e., the system, which is monitored using the monitoring method. At the same time, the monitoring method permits a reliable diagnosis of an existing abnormal operating state.

In accordance with one embodiment of the inventive monitoring method, the second, third and/or fourth step can be performed separately for zero correlations and operating correlations. In particular, the second, third and/or fourth step can be performed for the zero correlations with an adjustable first frequency. Further, the second, third and/or fourth step can be performed for the operating correlations with an adjustable second frequency. The first or second frequency can be specified by a user or an algorithm. Furthermore, the first frequency can be lower than the second frequency. The inventive monitoring method can hence be adapted to different applications, in which an abnormal operating state is expected to be more easily identified via the operating correlations or the zero correlations. Overall, the inventive monitoring method has a broad range of uses. Further, the second, third and/or fourth step can alternatively be executed in a first pass for the operating correlations. If an abnormal operating state is identified in the first pass, the second, third and/or fourth step can be performed for the zero correlations. Here, separate network deviation parameters are determined in the first and second pass and are matched to respectively associated adjustable network threshold values. The inventive monitoring method can thus be implemented with reduced computing power.

In a further embodiment of the inventive monitoring method, a fifth step is provided, in which an edge of the neural network, which in a normal operating state of the system corresponds to a zero correlation, is identified as a defective edge. The edge is identified as a defective edge if the amount of its correlation value exceeds the associated correlation threshold value. The fifth step is performed if the abnormal operating state of the system is identified in the fourth step. The amount by which the correlation threshold value is exceeded is found by a separate comparison of the correlation values with the corresponding correlation threshold value. As a result, compute-intensive comparison operations are then performed only if, based on the exceeded network threshold value, it is to be expected that at least one correlation threshold value is exceeded and frequent unsuccessful passes of compute-intensive operations can be prevented. The inventive monitoring method consequently offers a rational way of using the computing power employed. At the same time, the inventive monitoring method offers a targeted diagnosis.

In addition, the correlation threshold value of at least one edge in the neural network can be designed as a fixed threshold value or as a moving threshold value. A fixed threshold value offers simple configurability of the monitoring method. In the case of correlation threshold values that are standardized to a reference value, the inventive monitoring method can easily be configured by at least one fixed threshold value, for example, during an initialization.

In contrast, a moving threshold value for example enables account to be taken of a degradation effect on a device, and thus on a corresponding edge of the neural network. The moving threshold value can for example be formed by a variable total reconstruction error. For example, the correlation threshold value can increase or decrease along a function depending on the number of hours a device has been operating. As a result, inappropriate warnings are prevented and/or premature degradations of devices are reliably identified. The diagnostic accuracy of the inventive monitoring method is thus further increased.

Furthermore, the inventive monitoring method can have a sixth step, in which pattern matching is performed based on the defective edge identified, for such as in the fifth step. In the sixth step, the defective edge is captured and is evaluated using pattern matching. With the pattern matching the cause of the defect is identified in the sixth step. To this end, a database containing a large number of stored comparison patterns of different damage states, i.e., abnormal operating states of the system, can be employed. Alternatively or additionally, the pattern matching can also be performed via artificial intelligence, for example, a machine-learning algorithm, which is trained before and/or during the operation of the system. During pattern matching, it is also possible to take account for one or more defective edges of the extent to which, i.e., in which amount, these exceed the amount of the associated correlation threshold value. The cause of the defect can, for example, be a defective device in the system, a loss of a functionality of such a device or an external influence on the system. The inventive monitoring method can be performed with reduced computing power or can be performed quickly with increased computing power. As a result, such artificial intelligence can be further developed, in particular further trained, concurrently with the operation of the system. The inventive monitoring method thus offers an improved identification of abnormal operating states of the system.

The objects and advantages are similarly achieved by an inventive computer program product, i.e., a computer readable medium, such as a RAM, ROM, EEPROM, CD-ROM or, or any other media that can be used to carry or store desired program code in the form of instructions or data structures and that can be accessed by a computer. The computer program product is configured to receive measured values and/or control signals from devices in a system, to store them at least temporarily and to process them. The computer program product is also configured to issue a warning to a user and/or an electronic warning signal. The computer program product serves to monitor the system to which the devices belong and for the operation of which they interact. The measured values and/or control commands are processed in connection with a monitoring method, which can run concurrently, i.e., essentially in parallel, in particular in real time, with the operation of the system. In accordance with the invention, the computer program product is configured to perform a monitoring method in accordance with at least one of the disclosed embodiments outlined above. The computer program product can be configured to be monolithic, i.e., to operate on a single hardware platform. Alternatively, the computer program product can be designed to be modular, i.e., to comprise subprograms that can be executed on separate hardware platforms, for example, a computer cloud, and interact via a communicative data connection in order to execute the respective monitoring method. The inventive computer program product enables the inventive monitoring method easily to be implemented.

The underlying objects and advantages are also achieved by an inventive monitoring unit for a system, where the monitoring unit can include a processor and memory. The monitoring unit is configured to monitor operation of the system to which it is at least functionally coupled, and to issue a warning. The system to be monitored comprises a plurality of devices that interact to operate the system and for which measured values and/or control commands can be captured. The capture of the measured values and/or control commands, which also comprises receipt, is here performed by the monitoring unit. The monitoring unit is also configured to process the captured measured values and/or control commands. In accordance with the invention, the monitoring unit is configured to process the measured values and/or control commands via a computer program product, with which the monitoring unit is equipped. The computer program product is inventively configured in accordance with one of the disclosed embodiment presented above.

The objects and advantages are further achieved by an inventive gas analysis device. The gas analysis device comprises a plurality of devices that interact to condition and measure a material sample. In particular, the gas analysis device can be configured to determine a composition of the material sample at least qualitatively. The gas analysis device is provided with a monitoring unit that is coupled to a plurality of devices. The monitoring unit is configured to identify an abnormal operating state of the gas analysis device. In accordance with the invention, the monitoring unit is configured in accordance with one of the disclosed embodiment presented above.

The objects and advantages are further achieved by an inventive use of artificial intelligence, which is configured to monitor a gas analysis device. The artificial intelligence is suitable for receiving measured values and/or control commands from devices of the gas analysis device directly or indirectly and for processing them. The use of artificial intelligence comprises at least the issue of a warning, which can, for example, be a visual or acoustic warning to a user and/or an electronic warning signal. In order to monitor the gas analysis device, the artificial intelligence is designed to perform a monitoring method. In accordance with the invention, the monitoring method can be configured in accordance with the disclosed embodiments. The use of artificial intelligence can in particular comprise the operational sequence of a correspondingly designed computer program product, as presented above, for example.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention is explained in greater detail below in figures using individual forms of embodiment. The figures are to be read as complementary to one another in that the same reference characters in different figures have the same technical meaning. The features of the individual forms of embodiment can also be combined with one another. Furthermore, the forms of embodiment shown in the figures can be combined with the features outlined above, in which.

DETAILED DESCRIPTION OF THE EXEMPLARY EMBODIMENTS

Figure 1:
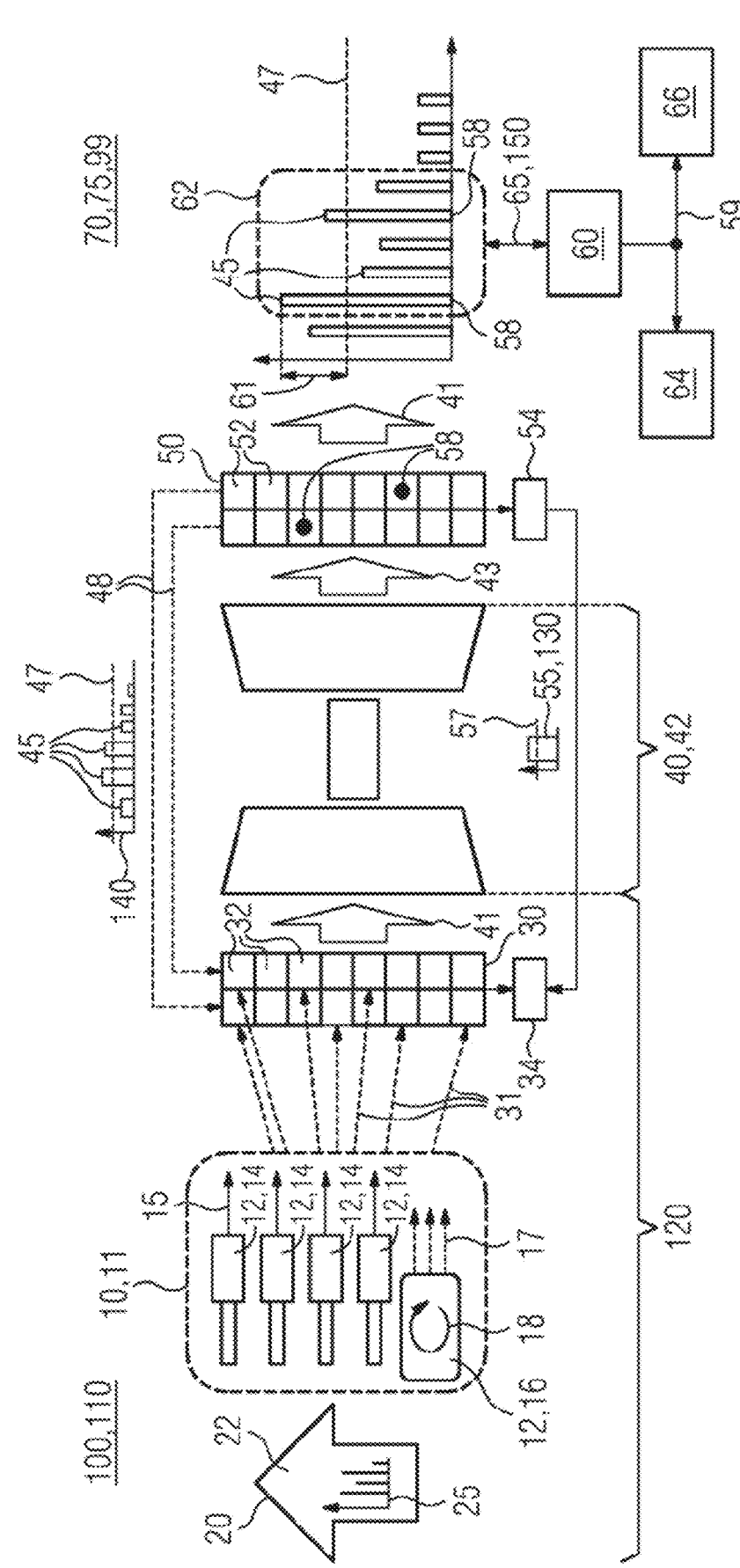
FIG. 1 schematically shows an operational sequence of a first embodiment of the inventive monitoring method.

A first embodiment of the inventive monitoring method 100 is represented schematically in FIG. 1. The monitoring method 100 serves to monitor a system 10 with which a system process 20 is performed. The system 10 is configured as a gas analysis device 11 and the system process 20 performed thereon comprises determining a composition 25 of a material sample 22. To this end, the system 10 is equipped with a plurality of devices 12 that are formed as sensors 14 or as a control unit 14. The control unit 16 is configured to influence the system process 20 via a running control program 18. The sensors 14 capture physical variables relevant to the system process 20. The sensors 14 are configured to output measured values 15 and the control unit 14 is configured to output control commands 17. The first embodiment shown in FIG. 1 assumes that a first step 110 has been concluded, in which an input signal array 30 is provided with a plurality of cells 32. Also in the first step 110, a monitoring data array 50 is provided, which has a plurality of cells 52. The cells 52 of the monitoring data array 50 and the cells 32 of the input signal array 32 correspond to one another, so that the input data array 32 and the monitoring data array 52 are identical in terms of structure.

In the first embodiment of the monitoring method 100, a second step 120 occurs, in which the system 10 is provided in an active operating state, in which measured values 15 are provided by the sensors 14 and/or control commands 17 for the input signal array 30 by the control unit 16. The provision 31 of the measured values 15 or of the control commands 17 is implemented by storing them separately in a cell 32 of the input data array 30. Also performed is a provision 41 of the input signal array 30 to a further processing unit 40, which is formed as an autoencoder 42. With the further processing unit 40, a third step 130 of the monitoring method 100 is performed.

With the further processing unit 40 contents, i.e., values, for cells 52 of the monitoring data array 50 are determined based on the input signal array 30. Using this, a comparison value 54 of the monitoring data array 50 is in turn determined, which combines the contents of its cells 52. A comparison value 34 of the input signal array 30 is also determined, which also combines the contents of its cells 32. The comparison values 34, 54 can, for example, each be formed as a sum. Further, by matching the comparison values 34, 54 of the input signal array 30 and the monitoring data array 50, a system deviation parameter 55 is determined. The system deviation parameter 55 is a total reconstruction error and represents in compact form an overall state of the system 10. In the third step 130, the system deviation parameter 55 is further compared with a system threshold value 57. If the amount of the system deviation parameter 55 exceeds the system threshold value 57, then an abnormal operating state of the system 10 is identified. The abnormal operating state identified in the third step 130 is nonspecific, i.e., is not suitable for indicating an underlying cause of a defect. If the abnormal operating state of the system 10 is identified in the third step 130, then a fourth step 140 follows during the inventive monitoring method 100.

In the fourth step 140, the contents of cells 52 of the monitoring data array 50 are compared separately, i.e., individually, with the contents of cells 32 of the input signal array 30. In a normal operating state of the system 10, the further processing unit 40, configured as an autoencoder 42, maps the contents of the cells 32 of the input signal array 30 essentially identically as contents into the cells 52 of the monitoring data array 50. The mapping 43 is implemented by storing contents cell by cell. Accordingly, in the fourth step 140, a cell deviation parameter 45 is determined separately for a plurality of cells 32 of the input signal array 30 and corresponding cells 52 of the monitoring data array 50. The cell deviation parameter 45 can, for example, be determined by a difference between the associated cells 32, 53. The cell deviation parameters 45 determined in this way are each compared to an adjustable cell threshold value 47. Such a comparison is symbolized in FIG. 1 by the arrows 48. If the amount of a cell deviation parameter 45 exceeds the associated adjustable cell threshold value 47, then the associated cell 32, 52 of the input signal array 30 or of the monitoring data array 50 is identified as a defective cell 58. To this end, the defective cells 58 are marked accordingly, for example, with what is known as a signature bit.

Furthermore, in the monitoring method 100 a fifth step 150 occurs, for which the contents of the cells 52 of the monitoring data array 50 are provided for matching with a database 60. The provision for the fifth step 150 is represented in FIG. 1 by an arrow 41. In the fifth step 150, an overrun 61 is determined for at least one defective cell 58, by which the amount of the contents of the defective cell 58 exceeds the associated cell deviation parameter 45. The cells 32, 52 of the monitoring data array 50 or of the input signal array 30 that exceed the amount of the corresponding cell threshold value 47 are further captured. This results, for example, in connection with cell deviation parameters 45, the amount of which undershoots the associated cell threshold value 47, in a pattern 62 that is characteristic of an underlying cause of the defect. The pattern 62 is identified in the fifth step 150 by pattern matching 65 via the database 60. Stored in the database 60 is a plurality of patterns 62 that serve as comparison patterns. If a pattern 62 is identified in the fifth step 150, then a corresponding warning 59 is issued. The warning 59 can show the presence of the abnormal operating state of the system 10, indicate a defective device 12 associated with at least one defective cell 58, and/or can indicate the identified cause of the defect. The warning 59 can be supplied to a display unit 64, which is configured to issue the warning 59, for example, as a visual or an acoustic warning to a user. Alternatively or additionally, the warning 59 can be formed as an electronic warning signal, which is issued to a communication interface 66 that can be connected to a higher-level control unit, not shown in greater detail. The monitoring method 100 in FIG. 1 is implemented by a computer program product 70 which is executed on a monitoring unit 75. The computer program product 70 forms an artificial intelligence 99, which is used to monitor the system 10 configured as a gas chromatograph 11.

Figure 2:
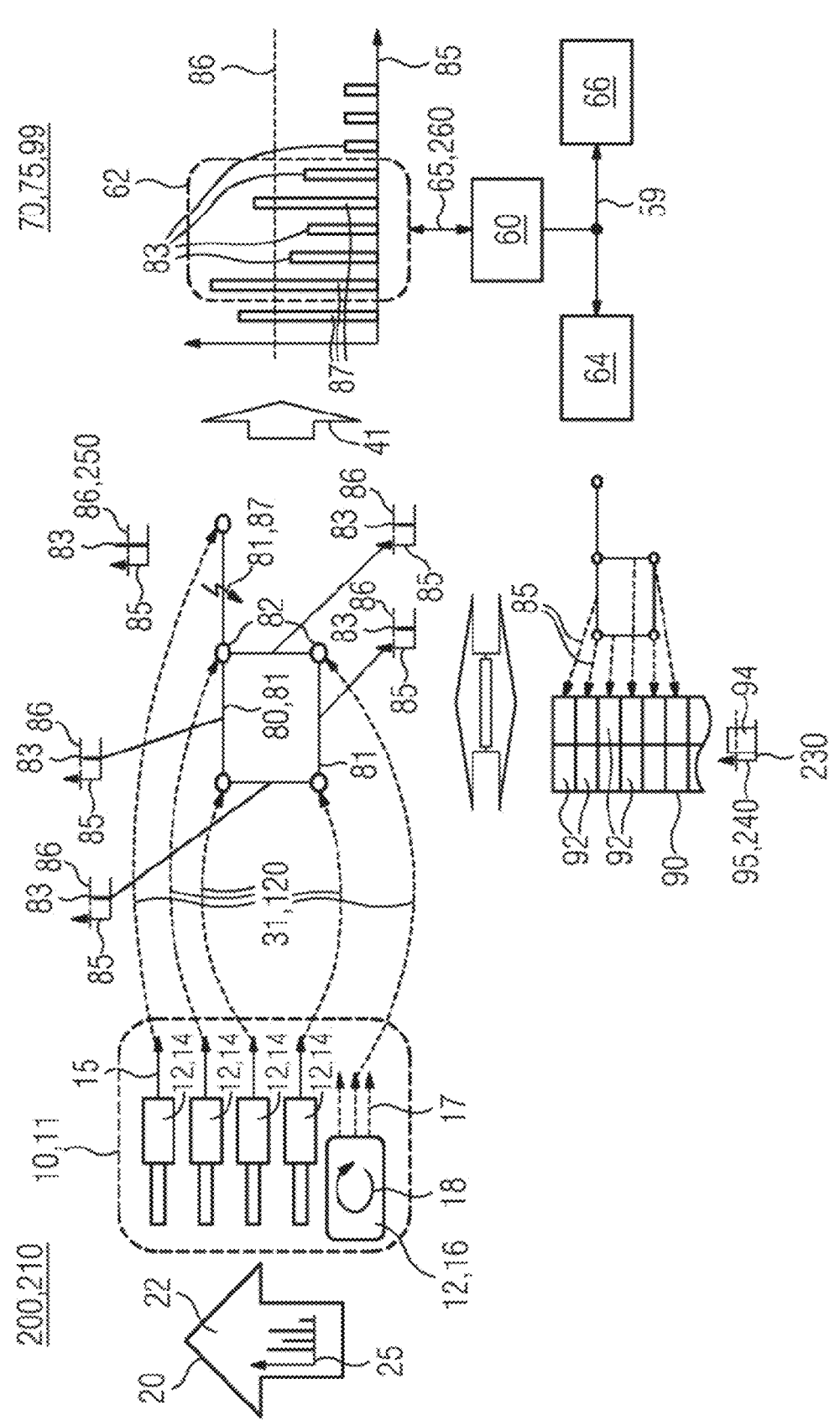
FIG. 2 schematically shows an operating sequence of a second embodiment of the inventive monitoring method.

A second embodiment of the inventive monitoring method 200 is depicted schematically in FIG. 2. The monitoring method 200 serves to monitor a system 10 with which a system process 20 is performed. The system 10 is configured as a gas analysis device 11 and the system process 20 performed thereon comprises determining a composition 25 of a material sample 22. To this end, the system 10 is equipped with a plurality of devices 12 that are formed as sensors 14 or as a control unit 14. The control unit 16 is configured to influence the system process 20 via a running control program 18. The sensors 14 capture physical variables relevant to the system process 20. The sensors 14 are configured to output measured values 15 and the control unit 14 is configured to output control commands 17.

The second embodiment shown in FIG. 2 assumes that a first step 210 has been concluded, in which a neural network 80 is provided that is trained for use in the monitoring method 200. The neural network 80 comprises a plurality of nodes 82, which are connected to one another via edges 81. Each edge 81 is assigned a correlation value 83, which reflects the extent to which a change at a node 82, i.e., a measured value 15 or control command 17 present there, follows a node 82 connected via the corresponding edge 81. The correlation threshold values 83 can, for example, be adjusted by a user input, a value table or an algorithm, in particular artificial intelligence. The edges 81 in the neural network 80 in accordance with FIG. 2 are mapped in a normal operating state of the system 10 as zero correlations 85. Accordingly, the amounts of the correlation values 83 of the corresponding edges 81 lie below an adjustable correlation threshold value 86, which essentially describes a minimum of interaction between the corresponding nodes 82. The zero correlations 85 in the neural network 80 thus describe measured values 15 or control commands 17, between which in the normal state not even an apparent connection exists. The edges 81 that correspond to zero correlations 85 are determined in the first step 210 by training the neural network 80.

The monitoring method 200 comprises a second step 220, which builds on the completed first step 210. In the second step 220, the system 10 is provided in an active operating state, in which the system process 20 is performed and the devices 12, i.e., the sensors 14 and the control unit 16, generate and provide measured values 15 or control commands 17. The provision 31 is symbolized in FIG. 2 by arrows. The measured values 15 or the control commands 17 each correspond to a node 82 and/or an edge 81 of the neural network 80 and supplied to the neural network 80 as input values. A third step 230 follows in which, based on the measured values 15 or 26 provided in the second step 220, the correlation values 83 present at the respective edges 81 are determined, i.e., calculated. The correlation values 83 present are, for example, stored in cells 92 of a table 90 and based on this a network deviation parameter 94 is determined. The network deviation parameter 94 can, for example, be formed as a sum of amounts of the correlation values 83. The network deviation parameter 94 is a measure of the presence of an unspecified abnormal operating state of the system 10. The monitoring method 200 further comprises performing a fourth step 240. In the fourth step 240, the network deviation parameter 94 determined in the third step 230 is compared to a network threshold value 95. In a normal operating state of the system 10, the amount of the network deviation parameter 94 undershoots the network threshold parameter 95. The network threshold value 95 can be established as a fixed threshold value or as a moving threshold value, which can, for example, increase, taking into account the operating hours completed by the system 10. If the presence of an abnormal operating state is identified, then a warning can be issued.

Furthermore, a fifth step 250 belongs to the monitoring method 200 in accordance with FIG. 2, in which the correlation values 83 of the individual edges 81 are compared to the associated correlation threshold values 86. If the amount of the correlation value 83 of an edge 81 exceeds the associated correlation threshold value 86, then the associated edge 81 is identified as a defective edge 87. The defective edge 87 enables a conclusion to be drawn that the measured value 15 or control command 17 at one of the nodes 82 that are connected by the edge 81 has arisen as a result of an abnormal operating state of the system 10. Accordingly, it is possible to diagnose that a device 12 belonging to the corresponding node 82 is defective or at least can be expected to be defective.

In addition, the monitoring method 200 comprises a sixth step 260, in which at least the correlation values 83 are provided for a further evaluation. The provision 41 is represented by an arrow in FIG. 2. In the sixth step 260, a pattern 62, which comprises a plurality of correlation values 83 present, is determined based on the at least one identified defective edge 81. To this end, the correlation values 83 of a plurality of edges 81 are compared jointly, i.e., essentially simultaneously, to the respectively associated correlation threshold value 86, which are zero correlations 85 in the normal operating state. Characteristic patterns 62 emerge for the respective incidence of a defect from the amounts of the correlation values 83, and how much these where appropriate exceed the associated correlation threshold value 86. The patterns 62 are identified in the sixth step 260 via a database 60, with which pattern matching 65 is performed. Accordingly, the cause of a defect is diagnosed via the pattern matching 65. If a pattern 62 is identified in the sixth step 260, then a corresponding warning 59 is issued. The warning 59 can show the presence of the abnormal operating state of the system 10, indicate a defective device 12 associated with the defective edge 81, and/or indicate the identified cause of the defect. The warning 59 can be passed to a display unit 64 that is configured to output the warning 59, for example, as a visual or acoustic warning to a user. Alternatively or additionally, the warning 59 can be formed as an electronic warning signal that is issued to a communication interface 66, which can be connected to a higher-level control unit, not shown in greater detail. The monitoring method 200 in FIG. 2 is implemented by a computer program product 70 which is executed on a monitoring unit 75. The computer program product 70 forms an artificial intelligence 99, which is used to monitor the system 10 configured as a gas chromatograph 11.

Figure 3:
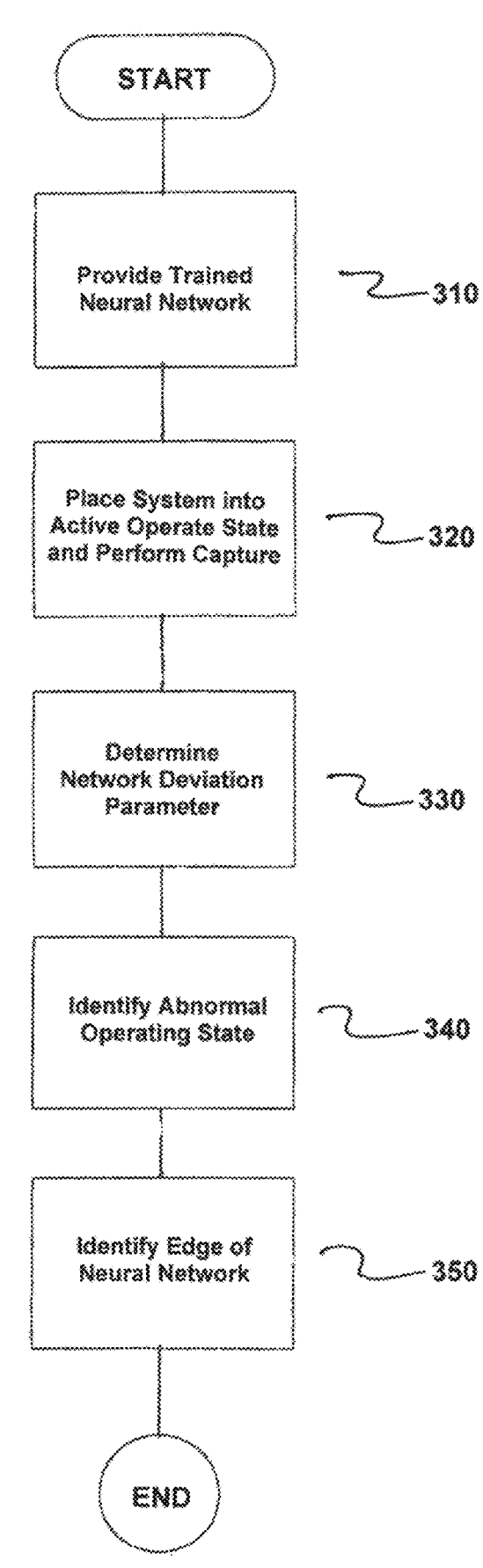
FIG. 3 is a flowchart of the method in accordance with the invention.

FIG. 3 is a flowchart of the monitoring method 200 for a system 10 having a plurality of devices 12, which form nodes 82 in a neural network 80, which maps an interaction of the devices 12 in the system 10.

The method comprises a) providing a trained neural network 80 having a plurality of edges 81 that each correspond to a zero correlation 85 or an operating correlation, as indicated in step 310. Here, a correlation value 83 is determined during training for zero correlations 85, where the correlation value 83 has a value that is below an adjustable correlation threshold value 86.

Next, b) the system 10 is placed into an active operating state and at least one of measured values 15 and control commands 17 are captured, as indicated in step 320. In accordance with the method, each measured value 15 and control command 17 corresponds to at least one node 82 and/or at least one edge 81 of the neural network 80.

Next, c) a network deviation parameter 94 that combines correlation values 83 of a plurality of edges 81 of the neural network 80 is determined, as indicated in step 330. In accordance with method, the correlation values 83 are determined using at least one of the measured values 15 and control commands 17 captured during step 320.

Next, d) an abnormal operating state of the system 10 is identified, if a value of the network deviation parameter 94 exceeds an adjustable network threshold value 95, as indicated in step 340. Here, a warning 59 is issued if the abnormal operating state is identified.

Next, a) an edge 81 of the neural network 80 that corresponds to the zero correlation 85 in a normal operating state as a defective edge 87 is identified, if a value of the correlation value 83 associated with the identified edge 81 exceeds the associated correlation threshold value 86, as indicated in step 350.

Thus, while there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps that perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A monitoring method for a gas analyzer having a plurality of devices, which form nodes in a neural network, which maps an interaction of the devices in the gas analyzer, the method comprising:

a) providing a trained neural network having a plurality of edges which each correspond to a zero correlation or an operating correlation, a correlation value being determined during training for zero correlations, and the correlation value having a value which is below an adjustable correlation threshold value;

b) placing, by a controller, the gas analyzer into an active operating state and capturing, by the controller, at least one of measured values and control commands, each measured value and control command corresponding to least one of (i) at least one node and (ii) at least one edge of the neural network;

c) determining, by the controller, a network deviation parameter which combines correlation values of a plurality of edges of the neural network, the correlation values being determined utilizing at least one of the measured values and control commands captured during step b);

d) identifying, by the controller, an abnormal operating state of the system, if a value of the network deviation parameter exceeds an adjustable network threshold value, a warning being issued if the abnormal operating state is identified; and e) identifying an edge of the neural network which corresponds to the zero correlation in a normal operating state as a defective edge, if a value of the correlation value associated with the identified edge exceeds the associated correlation threshold value; and f) initiating a countermeasure during the active operating state of the gas analyzer to increase an efficiency of error detections within the gas analyzer based on a reduced computational load when the value of the correlation value associated with the identified edge exceeds the associated correlation threshold value such that the identified edge of the neural network which corresponds to the zero correlation in the normal operating state is identified as a defective edge.

2. The monitoring method as claimed in claim 1, wherein at least one of steps b), c) and d) are performed, by the controller, with a first frequency for operating correlations and are performed with a second frequency for zero correlations.

3. The monitoring method as claimed in claim 1, wherein at least one of steps b), c) and d) are performed, by the controller, in a first pass for operating correlations and in a second pass for zero correlations, if an abnormal state is identified in the first pass.

4. The monitoring method as claimed in claim 1, wherein at least one of steps b), c) and/or d) are performed, by the controller, in a first pass for operating correlations and in a second pass for zero correlations, if an abnormal state is identified in the first pass.

5. The monitoring method as claimed in claim 1, wherein the correlation threshold value is established as a fixed threshold value or as a moving threshold value.

6. The monitoring method as claimed in claim 2, wherein the correlation threshold value is established as a fixed threshold value or as a moving threshold value.

7. The monitoring method as claimed in claim 3, wherein the correlation threshold value is established as a fixed threshold value or as a moving threshold value.

8. The monitoring method as claimed in claim 1, the monitoring method further comprising:

f) performing, by the controller, a pattern matching and based on at least one identified defective edge and identifying a cause of a defect.

9. A non-transitory computer readable medium encoded with a computer program which, when executed by processor of a monitoring unit for monitoring a gas analyzer which has a plurality of devices which interact to operate the gas analyzer, causes at least one of measured values and control commands to be captured and processed, the program comprising:

a) program code for establishing a trained neural network having a plurality of edges which each correspond to a zero correlation or an operating correlation, a correlation value being determined during training for zero correlations, said correlation value have a value which is below an adjustable correlation threshold value;

b) program code for placing, by a controller, the gas analyzer into an active operating state and capturing at least one of measured values and control commands, each measured value and control command corresponding to least one of (i) at least one node and (ii) at least one edge of the neural network;

c) program code for determining, by the controller, a network deviation parameter which combines correlation values of a plurality of edges of the neural network, the correlation values being determined utilizing at least one of the measured values and control commands captured during step b);

d) program code for identifying, by the controller, an abnormal operating state of the gas analyzer, if a value of the network deviation parameter exceeds an adjustable network threshold value, a warning being issued if the abnormal operating state is identified; and e) program code for identifying an edge of the neural network which corresponds to the zero correlation in a normal operating state as a defective edge, if a value of the correlation value associated with the identified edge exceeds the associated correlation threshold value;

wherein a countermeasure is initiated during the active operating state of the gas analyzer increase an efficiency of error detections within the gas analyzer based on a reduced computational load when the value of the correlation value associated with the identified edge exceeds the associated correlation threshold value such that the identified edge of the neural network which corresponds to the zero correlation in the normal operating state is identified as a defective edge.

10. A monitoring unit for gas analyzer which comprises the plurality of devices which interact to operate the gas analyzer and for which measured values and/or control commands can be captured, wherein the monitoring unit is configured to receive and process at least one of the measured values and control commands and is configured to issue a warning, and wherein the monitoring unit includes the non-transitory computer readable medium as claimed in claim 9 to at least one of process the measured values and control commands.

11. The gas analyzer comprising the plurality of devices for conditioning and measuring a material sample, the gas analyzer being configured with the monitoring unit and identifying an abnormal operating state of the gas analyzer, wherein the monitoring unit is configured in accordance with claim 10.

* * * * *